(12) United States Patent
Madau et al.

(10) Patent No.: US 10,139,320 B2
(45) Date of Patent: Nov. 27, 2018

(54) COMPOSITION FOR PROCESSING HISTOLOGICAL, POSTMORTEM, CYTOLOGICAL SAMPLES

(71) Applicants: Giacomo Madau, Cagliari (IT); Abdelkrim Harchi, Castelnuovo del Garda (IT); Giorgio Rolesu, Ussana (IT); Adriano Viale, Rovigo (IT)

(72) Inventors: Giacomo Madau, Cagliari (IT); Abdelkrim Harchi, Castelnuovo del Garda (IT); Giorgio Rolesu, Ussana (IT); Adriano Viale, Rovigo (IT)

(73) Assignees: Giacomo Madau, Cagliari (IT); Abdelkrim Harchi, Castelnuovo del Garda (IT); Giorgio Rolesu, Ussana (IT)

( * ) Notice: Subject to any disclaimer, the term of this patent is extended or adjusted under 35 U.S.C. 154(b) by 365 days.

(21) Appl. No.: 14/388,754

(22) PCT Filed: Mar. 25, 2013

(86) PCT No.: PCT/IT2013/000088
§ 371 (c)(1),
(2) Date: Sep. 26, 2014

(87) PCT Pub. No.: WO2013/144986
PCT Pub. Date: Oct. 3, 2013

(65) Prior Publication Data
US 2015/0050652 A1  Feb. 19, 2015

(30) Foreign Application Priority Data

Mar. 30, 2012 (IT) .............. CA2012A0004
Nov. 21, 2012 (IT) .............. RM2012A0583

(51) Int. Cl.
| | | |
|---|---|---|
| *G01N 1/02* | (2006.01) | |
| *G01N 1/30* | (2006.01) | |
| *A01N 37/10* | (2006.01) | |
| *G01N 1/31* | (2006.01) | |

(52) U.S. Cl.
CPC .............. *G01N 1/30* (2013.01); *G01N 1/31* (2013.01); *G01N 2001/307* (2013.01)

(58) Field of Classification Search
CPC .................... G01N 1/30; G01N 1/02

USPC ................ 514/544, 549; 435/40.5
See application file for complete search history.

(56) References Cited

U.S. PATENT DOCUMENTS

| | | | |
|---|---|---|---|
| 4,263,278 A * | 4/1981 | Saurino ............ | A01N 1/00 424/75 |
| 4,425,328 A | 1/1984 | Nabial | |
| 8,278,068 B2 * | 10/2012 | Vielhaber et al. ....... | 435/70.3 |
| 2012/0171149 A1 * | 7/2012 | Battermann ......... | A61K 8/585 424/70.122 |
| 2013/0251663 A1 * | 9/2013 | Berry et al. ................. | 424/75 |

FOREIGN PATENT DOCUMENTS

| | | | |
|---|---|---|---|
| DE | 10221335 | 11/2003 | |
| DE | 102011013341 | 12/2011 | |
| EP | 0653617 A2 | 5/1995 | |
| EP | 0822403 | 2/1998 | |
| EP | 1508026 | 2/2005 | |
| EP | 1 276 372 B1 * | 10/2005 | ........... A01N 25/02 |
| EP | 1977214 A2 * | 10/2008 | ........... G01N 1/30 |
| GB | 2090613 | 7/1982 | |
| WO | 95/17657 A1 | 6/1995 | |
| WO | 03/100384 A1 | 12/2003 | |
| WO | 03100384 | 12/2003 | |
| WO | WO 2006/059126 A1 * | 6/2006 | ........... A01N 1/00 |
| WO | 2006128622 | 12/2006 | |
| WO | 2007/084429 A2 | 7/2007 | |
| WO | 2008112993 | 9/2008 | |

OTHER PUBLICATIONS

Wikipedia "Formaldehyde" retrieved from https://en.wikipedia.org/wiki/Formaldehyde. Downloaded from the internet Dec. 25, 2015. 12 pages.
Written Opinion for PCT Application No. PCT/IT2013/000088 filed Mar. 25, 2013 on behalf of Madau Giacomo. dated Oct. 14, 2013. 7 pages.
International Search Report dated Oct. 14, 2013 for PCT/IT2013/00088 filed on Mar. 25, 2013 in the name of Madau Giacomo.

* cited by examiner

*Primary Examiner* — Shengjun Wang
(74) *Attorney, Agent, or Firm* — Steinfl + Bruno, LLP

(57) ABSTRACT

The present disclosure describes a composition for preparing histological, postmortem, cytological or similar samples for the analysis thereof, wherein the composition is not harmful, non-toxic, and able to rapidly produce dehydration and diaphonization of the biological samples.

8 Claims, No Drawings

COMPOSITION FOR PROCESSING HISTOLOGICAL, POSTMORTEM, CYTOLOGICAL SAMPLES

CROSS REFERENCE TO RELATED APPLICATIONS

The present application is the US national stage of International Patent Application PCT/IT2013/000088 filed on Mar. 25, 2013 which, in turn, claims priority to Italian Patent Application RM2012A000583 filed on Nov. 21, 2012 and Italian Patent Application CA2012A000004 filed on Mar. 30, 2012.

The present invention concerns a composition for processing histological, postmortem, cytological samples. Particularly, the invention concerns a composition for processing histological, postmortem, cytological samples or similar samples, said composition being not harmful and not toxic and being able to produce both dehydration and diaphanization of the biological samples shortly.

Pre-analytical procedures used in pathological anatomy provide for one stage of biological samples treatment (or processing stage), preliminary fixed in formalin, for example consisting of tissues or cells harvested by a patient or post-mortem, that permits to solidify the sample and cut the same in sections to be analyzed.

The processing phase of biological samples generally comprises the following stages: a) fixation stage; b) dehydration stage; c) diaphanization stage; d) embedding stage.

In the fixation stage anatomical parts, for example, deriving from operating theatres or autopsy rooms or surgical rooms, are immersed in a fixative fluid, in general buffered formalin 10% or alcohol or others specific fixatives depending on the peculiarity of the later histological or immunohistochemical analysis. The function of this stage is to stop protein denaturation preventing the detachment of protein chains. Therefore, fixation have the purpose to maintain tissue structure.

The dehydration stage consists of removing water (formalin is an aqueous solution of formaldehyde) from the biological sample and then embedding the same in paraffin, the latter being insoluble in water. This stage is carried out by immersing the sample in anhydrous water soluble solvent.

The diaphanization stage allows the biological sample to be embedded in paraffin hereafter. For this purpose solvents compatible with the impregnating agent (for example paraffin), which substitute the water soluble solvent in this stage, are used. For example, diaphanizing agents are paraffin solvents, xylene or xylene substitutes such as D-limonene, Isoparaffins, Octane, Acetone.

Finally, the sample is subjected to the stage of embedding in paraffin consisting in immersing the sample in paraffin melted at about 54-58° C. In this stage, the diaphanizing solvent contained in tissues is replaced by paraffin. After having included samples in a tile, sample cooling and solidification, that will allow to carry out the cut of the sections with microtome in the desired micron size for the observation with the microscope, are performed.

Currently sample processing is automatically carried out by means of devices which allow to program time of permanence, temperature, pressure and vacuum in each reagent. Generally stations are 12 or 15 and the average time of the whole processing stage is 12-18 hours. Time depends on the type of tissue. By means of the conventional standard method, the processing is carried out by steps in ethyl alcohol having an increasing gradation in order to dehydrate the biological tissue. The steps are carried out before in ethyl alcohol 50%, and then, in a subsequent step, in ethyl alcohol 70%, later in ethyl alcohol 80%, then in alcohol 90%, later three steps in alcohol 96% are carried out and three steps in anhydrous absolute alcohol 99.99%. At the end of this stage all the water in the tissue of the sample is replaced with ethyl alcohol.

The later steps correspond to the diaphanization stage having the purpose to replace the alcohol with a solvent compatible with paraffin. Generally in this stage Xylol or a substitute thereof is used and 3 steps in 3 different stations are carried out because there is the need that the tissue passes in another station with clean solvent after having released alcohol at the first step.

Finally, in the embedding stage the tissue is processed in 3 or 4 stations of paraffin fused at 54-58° C.

Summarizing, the state of the art, after fixing in 10% formalin, provides the following steps and times:

1.00 hour Alcohol 50%
1.00 hour Alcohol 70%
1.00 hour Alcohol 80%
1.00 hour Alcohol 96%
1.00 hour Alcohol 96%
1.30 hour Alcohol 99.99%
1.30 hour Alcohol 99.99%
1.00 hour Xylol or substitute
1.00 hour Xylol or substitute
1.30 hour Xylol or substitute
1.30 hour Paraffin
2.00 hour Paraffin
2.00 hour Paraffin.

Based on that described above, it is evident that known methods present several disadvantages: the use of different reagents, making necessary the preparation of increasing gradations of alcohol, xylol or substitutes thereof; the use of highly volatile solvents (alcohol o Xylol); the use of substances which cause allergies, such as xylol, toluol, octane, d-limonene, turpentine, acetone, isoparaffins, or which are harmful and in some cases toxic to operators, for example xylol, toluol, octane, acetone, isoparaffins; long times and numerous stations for the processing are provided.

Other methods of processing, which use a mixture of ethyl alcohol, isopropyl alcohol and hydrocarbons derived from crude oil, for example Octane or Isoparrafins in place of alcohol and xylol or a xylol substitute, are known. Particularly, EP0822403 and EP1508026 patents describe a method for tissue processing based on the use of a mixture which allows to carry out the dehydration and diaphanization of samples in the same time. Such mixture is constituted by octane (or isoparaffins), isopropyl alcohol and ethanol. However, even if these methods reduce the sample processing times, they present the serious disadvantages of using substances, such as octane or isoparaffins, having high volatility and noxiousness to operators and environment.

In the light of above, it is therefore apparent the need to provide new reagents able to overcome the disadvantages of known reagents.

The inventors of the present invention have now found that 2-ethylhexyl esters selected from the group consisting of 2-ethylhexyl benzoate, 2-ethylhexyl palmitate, 2-ethylhexyl cocoate, 2-ethylhexyl stearate, 2-ethylhexyl acetate, preferably 2-ethylhexyl benzoate, have diaphanizing capability. Therefore, the inventors have prepared a dehydrating and diaphanizing composition for processing biological samples to be subjected to analysis, said composition being without polycyclic aromatic hydrocarbons carcinogenic to humans. The composition according to the present invention, unlike known reagents, is neither noxious nor toxic to operators, in accordance with the European Directive on workers protection against risks deriving from exposure to chemical, physical and biological agents during work, and relating to the improvement of workers safety and healthy. Furthermore, the composition of the present invention presents low volatility always according to the European Directives on safety for the workplace and high biodegradability (about 88%) for an higher environment respect.

The use of the composition according to the present invention allows to reduce notably the sample processing times and simplify the stages of the processing. The composition according to the invention, in fact, replaces known reagents of the dehydration and diaphanization stages. Therefore, directly or after fixation in 10% formalin, the sample is processed with the composition of the invention, as unique reagent, avoiding the distinct phases of dehydration in ethyl alcohol and diaphanization in xylol and substitutes thereof. Furthermore, according to the method of the present invention, the processing stations are reduced to three with an average time of permanence in the reagent of 1.30 hour. More precisely, tissue processing, after the fixation, comprises three steps of the tissue in the same reagent in three different stations and then passing to the embedding phase in paraffin for 1.30 hour each.

Therefore, the time processing, with respect to the prior art, is reduced to about 9 hours for the complete processing, with respect to 15 or 18 hours of the conventional processing. An example of processing according to the present invention applied to a tissue with high percentage of lipid substance (therefore critical) and with a thickness of 4 mm, is reported below. Tissues with low percentage of lipid substance and with a thinner thickness led to a remarkable reduction of processing time and stations.

The processing by using the composition of the invention, after the fixation, may comprise the following stations and times:
1.30 hour Reagent object of the invention;
1.30 hour Reagent object of the invention;
1.30 hour Reagent object of the invention;
1.30 hour Paraffin;
1.30 hour Paraffin;
1.30 hour Paraffin.

As an alternative, for small biopsies, the method may comprise:
5 minutes Reagent object of the invention;
5 minutes Reagent object of the invention;
5 minutes Reagent object of the invention;
5 minutes Reagent object of the invention;
5 minutes Paraffin;
5 minutes Paraffin.

In the experimental trials in which the biological sample processing by utilizing the composition according to the present invention was used, an improvement of cellular structure of the tissue, namely a preservation of the diagnostic compound morphology and coloring was observed. For this reason, the fact that numerous comparative trials were carried out is to be highlighted, namely each sample was divided in more parts and one part of sample was subjected to a processing in accordance with the traditional method, whereas another part was subjected to a processing with the composition object of the present invention. Comparing the results obtained both by means of the traditional method and the composition object of the present invention, the result that the sample processed with the composition object of the present invention, after cut and coloring, appears clearer and better differentiated under a microscope, was demonstrated. The cellular structure appears more defined, hence allowing an easier reading and diagnostic interpretation. Further immunohistochemical tests, compared using the same times of treatment, were carried out (the same time of antigen retrieval, antibody incubation, detection system and cromogenic). As far as the positivity and negativity of antigen-antibody reaction are concerned, the results were overlapping, moreover, samples processed with the composition object of the present invention, presented a better chromogenic definition in the antigen-antibody positive sites at the microscope stage. Therefore, the processing according to the present invention makes the diagnosis more reliable, especially in cases in which, a quantitative analysis about the tissue area positivity is necessary to be carried out.

It is therefore specific object of the present invention a composition comprising or consisting of: a) at least one 2-ethylhexyl ester selected from the group consisting of 2-ethylhexyl benzoate, 2-ethylhexyl palmitate, 2-ethylhexyl cocoate, 2-ethylhexyl stearate, 2-ethylhexyl acetate; b) ethyl alcohol and/or isopropyl alcohol. Preferably, a mixture of ethyl alcohol with a low percentage of isopropyl alcohol is used, because of isopropyl alcohol is considered irritant and it is highly volatile, therefore using it a little is better. However, the sample may be processed even with a composition containing only ethyl alcohol and 2-ethylhexyl ester, preferably 2-ethylhexyl benzoate, or only isopropyl alcohol and 2-ethylhexyl ester, preferably 2-ethylhexyl benzoate.

In the composition according to the present invention, preferably, the concentration of 2-ethylhexyl ester, preferably 2-ethylhexyl benzoate, ranges from 30 to 70%, the concentration of ethyl alcohol ranges from 20 to 60% and the concentration of isopropyl alcohol ranges from 10 to 30%, in which said percentages are volume percentages with respect to the total volume of the composition. According to a preferred embodiment, the concentration of 2-ethylhexyl ester, preferably 2-ethylhexyl benzoate, is 50%, 35% of ethyl alcohol and 15% of isopropyl alcohol, wherein said percentages are volume percentages with respect to the total volume of the composition.

According to an alternative embodiment of the present invention, 2-ethylhexyl ester may be replaced by a mixture of diisobutyl or dimethyl glutarate at a concentration from 55 to 70%, diisobutyl or dimethyl adipate at a concentration from 10 to 30% and diisobutyl or dimethyl succinate at a concentration from 10 to 25%, wherein said percentages are volume percentages with respect to the total volume of the mixture of diisobutyl or dimethyl glutarate, adipate and succinate.

It is a further object of the present invention, the use of the as above defined composition for biological samples processing, for example histological, cytological, postmortem samples or similar. Said samples, after processing according to the present invention, may be subjected to microscopic analysis, immunoistochemical analysis, analysis based on ISH, FISH, CISH, PCR molecular biology techniques.

The present invention further concerns a method for processing biological samples comprising or consisting of the stage of biological sample treatment, such as an histological, cytological, postmortem samples or similar, with the as above defined composition. In accordance with the method of the invention, the sample treatment may be occurred at a temperature which ranges from 20-30° C. to 80° C. or at room temperature.

It is a further object of the present invention, the use of at least one 2-ethylhexyl ester selected from the group consisting of 2-ethylhexyl benzoate, 2-ethylhexyl palmitate, 2-ethylhexyl cocoate, 2-ethylhexyl stearate, 2-ethylhexyl acetate 2-ethylhexyl benzoate, preferably 2-ethylhexyl benzoate, as diaphanizing agent of biological samples.

The present invention now will be described by an illustrative, but not limitative way according to preferred embodiments thereof.

EXAMPLE 1

Processing of small biopsies (pulmonary, renal, hepatic) of about 1 mm in thickness and 1 cm in length.

The just carried out biopsy taking (TAC conducted, either by endoscopic or percutaneous way) is immediately immersed in the composition of the present invention (alcoholic mixture 50%+2-ethylhexyl benzoate 50%) for 1 hour (for 30 minutes whether the sample is already fixed in formalin). The whole processing comprises: 30 minutes of fixation, 3 steps of about 7 minutes each in the composition object of the invention, 2 steps of about 5 minutes each in paraffin melted at 58° C. Therefore the sample is embedded in paraffin and cut by microtome. Obtained sections are put on a stove at 60° for about 20 minutes. Later a preliminary coloring with Hematoxylin and Eosin is carried out (the coloring stage, comprised the assembling of the slide, has a standard duration of about 1 hour). Therefore the slide is viewed under a microscope.

Conclusions: from the moment of the biopsy taking to the moment of the diagnostic formulation (even if preliminary, but in any case morphological) only three hours, in the case of not "fixed" biopsies, are needed; about two hours and half in the case of biopsies arrived at the laboratory already "fixed in formalin 10%".

One part of the same biological samples was subjected to a processing with solutions containing isopropyl alcohol, ethyl alcohol and octane or, as an alternative, isoparaffins. The samples processed with the composition object of the invention showed an higher structure from both the morphological point of view and chromatic yield, after the histochemical coloring in Hematoxylin-Eosin. Therefore an higher definition of cell structure details could be observed. Furthermore, immunohistochemical tests showed that results were overlapping in relation to the positivity and negativity of antigen-antibody reaction. Moreover, the samples processed with the composition object of the invention, at the microscope stage, had a better definition of chromogenic in the positive antigen-antibody sites. Therefore, the processing according to the present invention makes the diagnosis more reliable, especially in those cases in which, for diagnostic purposes, a quantitative analysis about the tissue area positivity is necessary to be carried out.

EXAMPLE 2

Processing of a pulmonary tissue taking composed for about 50% in volume by apparently normal tissue and by tissue apparently not normal for the 50%, namely pathological (possible tumor) having parallelepiped shape of 1 cm×1 cm×0.5 cm in sizes.

The tissue sample just harvested in the operating theatre is reduced to the above cited sizes and immersed for 3 hours in the composition of the invention (alcoholic mixture 50%+2-ethylhexyl benzoate), in 3 steps of about 60 minutes.

Therefore the sample is immersed in paraffin for about 1 hour (2 steps of 30 minutes each), cut by microtome, put on stove for about 20 minutes and colored with Hematoxylin and Eosin (duration of the coloring about 1 hour).

Conclusions: from the taking in the operating theatre to the moment of the diagnostic formulation about 6 hours are needed, considering even the average times for transporting materials from the operating theatre to laboratories.

As in the previous case, samples were processed even with solutions containing isopropyl alcohol, ethyl alcohol and octane or as an alternative isoparaffins. The results with samples processed with the composition object of the invention were considered overlapping with respect to results obtained both with the composition containing octane and with the composition containing isoparaffins. The immunoistochemical tests showed, as previously, that samples processed with the composition object of the invention, at the microscope stage, had a better chromogenic definition in the positive antigen-antibody sites. Therefore, the processing according to the present invention makes the diagnosis more reliable, especially in cases in which, for diagnostic purposes, a quantitative analysis about the tissue area positivity is necessary to be carried out. The same test was carried out by the traditional processing and conclusions were the same, with morphological aspects and immunohistochemical reactions better clearly better in the case of processing with the composition object of the invention.

The invention claimed is:

1. A method to process a biological sample, the method comprising
   treating the biological sample with a composition to process the biological sample, the composition comprising
      at least one 2-ethylhexyl ester selected from the group consisting of 2-ethylhexyl benzoate, 2-ethylhexyl palmitate, 2-ethylhexyl cocoate, 2-ethylhexyl stearate, and 2-ethylhexyl acetate; and
      ethyl alcohol and/or isopropyl alcohol,
      wherein the at least one 2-ethylhexyl ester is in a concentration ranging from 30% to 70%, with respect to a total volume of the composition, the ethyl alcohol is in a concentration ranging from 20% to 60% with respect to the total volume of the composition and the isopropyl alcohol is in a concentration ranging from 10% to 30% with respect to the total volume of the composition.

2. The method of claim 1, wherein the concentration of 2-ethylhexyl ester is 50%, the concentration of ethyl alcohol is 35% and the concentration of isopropyl alcohol is 15%, wherein said percentages are volume percentages with respect to the total volume of the composition.

3. The method according to claim 1, wherein the biological sample is selected from the group consisting of a histological, cytological, and a postmortem sample.

4. The method according to claim 1, wherein the biological sample is a sample to be subjected to microscopic analysis, immunohistochemical analysis, or analysis based on ISH, FISH, CISH, PCR or other molecular biology techniques.

5. The method according to claim 1, wherein said treatment occurs at a temperature range from 30° C. to 80° C. or at room temperature.

6. The method according to claim 1, wherein said biological sample is selected from the group consisting of a histological, a cytological, and a postmortem sample.

7. The method according to claim 1, wherein the biological sample is a postmortem sample.

8. A method to diaphanize a biological sample, the method comprising:
   treating the biological sample with a composition comprising at least one 2-ethylhexyl ester selected from the group consisting of 2-ethylhexyl benzoate, 2-ethylhexyl palmitate, 2-ethylhexyl cocoate, 2-ethylhexyl stearate, 2-ethylhexyl acetate, and 2-ethylhexyl benzoate as a diaphanizing agent of biological samples, wherein the concentration of 2-ethylhexyl ester ranges from 30% to 70%.

* * * * *